(12) United States Patent
Volchek

(10) Patent No.: US 6,627,452 B1
(45) Date of Patent: Sep. 30, 2003

(54) METHOD FOR SCREENING DRUG PREPARATIONS

(76) Inventor: Igor Vladimirovich Volchek, 1 Zanevsky prospect, offices #253-255, Sankt Peterberg (RU), 195196

(*) Notice: Subject to any disclaimer, the term of this patent is extended or adjusted under 35 U.S.C. 154(b) by 0 days.

(21) Appl. No.: 09/937,637

(22) PCT Filed: Apr. 20, 2000

(86) PCT No.: PCT/EA00/00001

§ 371 (c)(1),
(2), (4) Date: Sep. 25, 2001

(87) PCT Pub. No.: WO00/65342

PCT Pub. Date: Nov. 2, 2000

(30) Foreign Application Priority Data

Apr. 27, 1999 (RU) .......................................... 99108889

(51) Int. Cl.⁷ ............................................... G01N 25/08
(52) U.S. Cl. ........................ 436/150; 436/149; 436/151; 436/63
(58) Field of Search .......................... 436/63, 149, 150, 436/151

(56) References Cited

FOREIGN PATENT DOCUMENTS

| DE | 3717337 | 12/1988 |
|----|---------|---------|
| DE | 4017818 | 12/1991 |
| DE | 4038898 | 6/1992 |
| RU | 2000739 | 10/1993 |
| RU | 2007117 | 2/1994 |
| RU | 2046341 | 10/1995 |
| RU | 2072100 | 1/1997 |
| SU | 741153 | 6/1980 |
| SU | 1540804 | 2/1990 |
| SU | 1806601 | 4/1993 |

*Primary Examiner*—Jean C. Witz
(74) *Attorney, Agent, or Firm*—Lilling & Lilling P.C.

(57) ABSTRACT

The invention relates to medicine, specifically, to methods for drug preparations screening, more specifically, to choosing a drug and its optimal dose to treat a particular patient.

It is suggested to choose a drug preparation basing on the results of culturing of whole heparinized patient's blood in the presence of aqueous solutions of drugs to be compared, to analyze the ratio of —SH and —SS groups in the cellular fraction of patient's blood after culturing, and to choose the drug that makes the greatest value of the given ratio.

The method allows decreasing the screening time down to a few hours and is useful in treatment of viral, cancerous, autoimmune, and other diseases.

2 Claims, No Drawings

METHOD FOR SCREENING DRUG PREPARATIONS

FIELD OF THE INVENTION

The present invention relates to medicine, in particular, to methods for screening drug preparations performed to choosing a drug and its optimal dosage for treatment of a particular patient.

DESCRIPTION OF THE PRIOR ART

In the current art, the conventional way to select a drug for a particular patient involves medical examination of the patient, comparison of the results of the examination with recommendations provided by pharmacopoeia, prescribing of a drug or drug combination, and correction of the prescription basing on observation of the patient's response (Methods of Experimental Chemotherapy: a Practical Guide. Ed. by N. G. Pershin, Moscow, 1971, 234 pp.—In Russian).

However, the time cost and unreliability of choosing a treatment methodology for a particular patient and a high degree of subjectivity made it expedient to search for novel, more objective methods for choosing drugs and their dosages for a particular patient suffering from a particular disease.

A method for screening of therapeutic drugs is disclosed in Russian Patent No 2 007 117 (IPC A 61 B 5/04, 1992), which involves positioning of investigator's hands over a patient and test substances and choosing the optimal drug basing on the temperature response of the investigator.

This method is sufficiently universal, however it is also somewhat subjective and insufficiently reliable.

Soviet and Russian Patents and Certificates of Authorship No 1 806 601 (IPC A 61 B 5/04476, 1990), No 1 540 804 (IPC A 61 B 10/00, 1987), No 2 000 739 (IPC A 61 B 5/02, 1991), and No 2 046 341 (IPC G 01 N 33/48, 1994) disclose methods for screening of therapeutic drugs for treatment of particular CNS disorders and viral, cancerous, and other diseases. The methods are based on administration of test drugs into patient's body or application of the drugs to tissue preparations or body fluids, distinguishing of significant parameters, measuring of these parameters for each test drug, and choosing the drug that causes the greatest effects on the chosen parameters as the optimal drug.

However, these methods are of a limited applicability and do not yield sufficiently reliable results where complex therapy is required.

A method for choosing a medicinal drug to treat cardiovascular deficiency has been disclosed that involves chemiluminescence analysis of venous blood after its incubation with the solutions of the drug at different concentrations and the choice of the dose of the drug that produces minimal chemiluminescence as the target dose. (Russian Patent No 2072100 CI of Jan. 20, 1997).

This method is also of a limited applicability.

SUMMARY OF THE INVENTION

The aim of the present invention is to provide a more rapid and universal method for screening of drug preparations.

To this end, it was suggested to perform screening basing on culturing of a sample of whole heparinized blood with aqueous solutions of test drugs at different doses, to determine the ratio of —SH and —SS groups in the cellular fraction of patient's blood after culturing, and to choose the drug at its dose that produces the greatest ratio of —SH and —SS groups as the optimal drug at the optimal dose. (In choosing the prescribed drug one should proceed from that the optimal drug and its optimal dose for treatment of a patient makes said ratio to be about 3.0, as experiments have shown.)

Blood culturing is typically performed for 1 h at a temperature maximally close to 37° C., the tested drugs being added at doses amounting to 1:5000 of their therapeutic doses.

The method is based on the hypothesis that blood sulfur-containing compounds are the most sensitive to factors of various etiologies associated with body diseases, so drugs capable of normalizing them are the most efficacious in treatment of these disease.

The major distinctions of the method provided by this invention are the use of whole blood for culturing, determination of a new parameter, i.e., the ratio of —SH groups and —SS groups in the cell fraction of blood, and the assumption of the optimal value of the parameter.

DETAILED DESCRIPTION OF THE INVENTION

The practice of the method for screening drug preparations involves the following:

Each test drug at its in vitro dosage calculated to amount to 1:5000 of its therapeutic dosage is added to a test tube containing I ml of heparinized whole blood obtained from a peripheral vein, respective vehicles being added to control tubes, and the mixtures are incubated for 1 h at 37° C. The incubation time may be optionally protracted up to 2 h, which allows some increase in the accuracy of the method, however, this is reasonable only when test results for different drugs are close to each other, or the drugs render small effects on the ratio of —SH and —SS groups.

The amounts of —SH groups and —SS groups and their ratio in the cell fraction of blood are determined mainly using the methods of direct (—SH) and reverse (—SS) amperometric titration.

For direct amperometric titration, 10 ml of venous blood is added to a test tube containing 1–2 drops of 5000 IU/ml heparin as an anticoagulant. Then the blood sample is dispensed as 1-ml aliquots into the required number of test tubes (usually 7–9), which depends upon the number of drugs to be tested and their dosages. The test drugs are added to the test tubes at dosages required (each in vitro dosage is calculated to amount to 1:5000 of respective therapeutical dosage), whereas respective vehicles are added to control tubes. Then the mixtures are incubated in a thermostat for 1 h at 37° C. After incubation, the test and control tubes are centrifuged for 5–7 min at 800 rpm, and plasma is removed. Then each cell fraction is hemolyzed in a 0.1% Trylon B (Na-EDTA) solution (pH=7.0), for which purpose 1 part of blood cells is mixed with 19 parts of the solution, the mixture is placed into a refrigerator (+4° C.–+5° C.), and after 30 min the mixture is centrifuged for 15 min at 6000 rpm to sediment lysed cells. The supernatant (hemolysate) is used further. Into a titration vessel (a 30–40 ml beaker) 25–30 ml of ammonia buffer is added. The beaker is placed onto a magnetic stirrer, a platinum electrode and the free end of a salt bridge are immersed into the test solution and connected to an ammeter, and a capsule with a magnet is placed onto the bottom of the beaker and driven to rotation at such a rate as to avoid the sputtering of the solution. After the ammeter pointer has stabilized, titration is started by adding of 0.05-ml or 0.1-ml portions of a $10^{-3}$ M AgNO$_3$ solution. After each consecutive portion, the pointer is allowed to stabilize, its position is recorded, and thereafter titration is continued. After the end point is achieved, each next portion of the titrating solution causes a sharp increase in electric current and the respective shift of pointer position toward greater values. After additional 4–5 check measurements, the titration procedure is stopped and its results are used to graphically determine the amount of silver nitrate required to titrate the solution, which makes the basis to calculate —SH group content.

For reverse amperometric titration, 25 ml of ammonia buffer is added to a titration vessel. The vessel is put onto the top of a magnetic stirrer, the indicator electrode and the end of the salt bridge connected to the reference electrode are immersed into the solution, the ammeter and magnetic stirrer are linked up to mains, the stirrer is switched on, and the following reagents are sequentially added to the buffer: 0.5 ml of $1\times10^{-4}$ M AgNO$_3$ solution, 0.2 ml of a hemolysate, and 200 mg of sodium sulfite.

The ammeter is switched on and, after its pointer has been stabilized (after about 3–5 min), titration of a test sample is started using a $5\times10^{-4}$ M unithiol solution added to the reaction mixture by 0.05 portions or 0.1 ml portions till the final volume of 0.5 ml is added. After titration is completed, the amount of unithiol required to titrate the sample is determined graphically, and the amount determined is used to calculate the amount of —SS groups. Finally, the ratio of —SH group and —SS group concentrations are calculated.

As a rule, the above methods are combined. After —SH group content determination by the above direct titration method has been completed, sodium sulfite is added to the same solution without interrupting its stirring, and —SS group content in the same sample is determined using the equimolar unithiol solution, the excess silver nitrate solution for the reverse titration being added to the reaction mixture not once but as several portions in the course of the direct titration.

Industrial Utility

The possibility to use the method for screening drug preparations provided by the present invention in treatment of diseases of various etiologies is demonstrated by the following Examples.

EXAMPLE 1

Patient B-ya E.V. Diagnosis: transverse colon cancer ($T_3N_0M_0$). Resection of the transverse colon has been performed. The effects of different doses of an antitumor and immunomodulating drug Ukrain (Nowicky Pharma, Austria) and an antihypoxant drug Oliphen (OOO Oliphen, Russia) on blood thiol-disulfide balance have been determined. The results are presented in the Table 1 below.

By our estimates, the optimal drug is Ukrain administered as a 5.0-mg unit doses because when the respective in vitro Ukrain dose was added, the —SH/—SS ratio increased from 2.00 to 3.00. The patient received 1 course of treatment with Ukrain before surgery and two courses after surgery, Ukrain being administered at the 5.0-mg dose every other day ten times during each treatment course. The findings of the histological investigation of the removed tumor are as follows: adenocarcinoma with mucus in glandular lumens, necrotic foci, and inflammatory infiltration of the stroma. For three years up to now the complete remission is observed and serum carcinoembryonic antigen (CEA) level stays normal (1.2 ng/ml on Dec. 27, 1996 and 1.1 ng/ml on Apr. 10, 1997, the norm being within 5 ng/ml).

EXAMPLE 2

Patient G-va N.V. Diagnosis: transverse colon cancer ($T_4N_2M_1$). The tumor was resected to alleviate intestinal obstruction. Peritoneal carcinomatosis was found during the operation.

The effects of Ukrain and Reaferon (NPO Vector, Russia) on blood thiol-disulfide balance have been determined (see Table 1).

By our estimates, the optimal drug is Ukrain administered as a 10.0-mg unit doses because when the respective in vitro Ukrain dose was added, the —SH/—SS ratio increased from 1.17 to 1.75. A course of treatment with Ukrain administered each other day intravenously at the 10.0-mg dose was provided (10 injections). After the first injection, a characteristic response to administration of the drug was evident (body temperature increase up to 37.9° C. and sweating) indicating the efficacy of the treatment. The response gradually abated in the course of subsequent injections and became minimal by the end of the treatment. The subjective feeling of the patient significantly improved, and laboratory tests revealed the normalization of serum CEA (1.7 ng/ml on Dec. 9, 1996 and 1.3 ng/ml on Dec. 27, 1996). Subsequently, the patient received two more courses of treatment with Ukrain, and the stabilization of the patient's condition for 8 months was evident.

EXAMPLE 3

Patient L-n B. A. Diagnosis: left breast cancer ($T_3N_2M_1$) with spine metastases (Th$_{12}$, L$_{1-2}$) after mastectomy. The patient received radiation treatment of her spine and 4 chemotherapy courses, Bonephos.

When the effects of Ukrain and Oliphen on blood thiol-disulfide balance were studied (see Table 1), it was noticed that with this patient the values of the —SH/—SS coefficient were low at all doses of the drugs, the optimal one being Ukrain at the dose of 5.0 mg per injection (the respective in vitro dose increased the —SH/—SS coefficient from 1.00 to 1.67). However, in accordance with the accepted protocol, in this case, Ukrain treatment involved 10-mg doses administered intravenously each other day (10 injections). After treatment course, the patient's condition did not improve, pain persisted, the level of CA15-3 oncomarker somewhat increased (38.3 U/ml on Jan. 14, 1997 and 42.6 U/ml on Feb. 4, 1997, the normal values being within 26.9 U/ml). Subsequently, the disease rapidly progressed.

EXAMPLE 4

Patient A-va Sh.O., aged 59. Diagnosis: esophageal cancer ($T_2N_xM_0$). Radiation therapy has been provided.

Studies of the effects of Ukrain and Cycloferon (an interferon inducer, NTTF Polysan) on thiol-disulfide balance revealed that the optimal effect was afforded by Ukrain at the dose of 5.0 mg (the respective dose of Ukrain added in vitro increased the —SH/—SS coefficient from 0.93 to 2.50). Two courses of treatment with Ukrain given at the 5.0-mg dose each other day (10 injections) were provided. Before the first and the second course oncological marker levels were normal, and after the second course the level of CAI 9–9 was noticed to decrease (on Jan. 24, 1997 CEA level was 0.53 ng/ml and CA19-9 level was 5.0 U/ml, on Dec 30, 1998 CEA level was 0.80 ng/ml and CA19-9 level was 23.9 U/ml, and on Jan. 27, 1999 CA19-9 level was 18.1

U/ml, its normal level being within 37 U/ml). For three years up to now the stabilization of the patient's condition has been evident. Gastroduodenoscopy performed on Dec. 22, 1998 revealed the ulceration of the lower third of the esophagus (a 0.3×0.5-cm ulcer under fibrin) and erosive esophagitis. Ultrasonic investigation of the abdomen provided no data indicating the generalization of the pathological processes.

EXAMPLE 5

Patient D-va S.V. Diagnosis: prolymphocytic non-Hodgkin lymphoma of the stomach ($T_3N_2M_0$). Subtotal resection of the stomach (Billroth-2 type) has been performed. The histological investigation of the removed tumor revealed prolymphocytic lymphoma, and a similar histological picture was found in lymphatic nodes of the major and minor gastric curvatures. When the effects of Ukrain and Oliphen on blood thiol-disulfide balance was studied, it was noticed (see Table 1) that, with this patient, the optimal drug was Oliphen at the unit dose of 0.5 (when the respective dose was added in vitro, the —SH/—SS coefficient increased from 2.00 to 3.12). Three courses of treatment with Oliphen given as one 0.5-g tablet thrice a day were provided, course duration being 1.5 months, and intervals between the courses being 2–3 months. During 5 years, the full clinico-hematological remission has been observed.

EXAMPLE 6

Patient K-n A. V. Diagnosis: chronic viral hepatitis B with no delta-agent (virus). Studies of the effects of Reaferon and Cycloferon on blood thiol-disulfide balance (see Table 1) showed that the optimal drug for this patient was Reaferon at the unit dose of $1×10^6$ U (the respective dose added in vitro increased the —SH/—SS ratio from 1.52 to 3.07). A course of treatment with Reaferon administered intramuscularly at the dose of $10^6$ U each third day for 6 months was provided. The treatment was associated with the normalization of ALT and AST activities, reversal of HBV DNA, HBeAg, and HBsAg, and a stable remission lasted for 8 months.

EXAMPLE 7

Patient P-va G.A. Diagnosis: Stage II seronegative rapidly progressing rheumatoid polyarthritis with involvement of humeral, ulnar, radiocarpal, metacarpal, phalangeal, coxofemoral, and talocrural articulations. The rating of functional activity of the patient was 3. Testing of the effects of Oliphen and Cycloferon on blood thiol-disulfide balance (see Table 1) revealed that the optimal drug for this patient was Cycloferon at the unit dose of 0.25 mg (the respective dose added in vitro increased the —SH/—SS ratio from 1.24 to 2.56). A course of treatment with Cycloferon was provided involving intramuscular administration of 2 ml of 2% solution on days 1, 2, 4, 6, 8, 10, 12, 14, 16, 18, and 20. The treatment allowed reduction of the required daily ibuprofen dose from 3 tablets (0.6 g) to 2 tablets (0.4 g) after day 5 from the onset of the treatment and to 1 tablet (0.2 g) after day 10 and to completely discontinue analgetic drug intake after day 16 because of amelioration of pain. The motor activity of the patient significantly increased. Laboratory tests showed BSR decrease from 39 to 24 mm/h and C-reactive protein decrease from rating "++" to rating "+".

TABLE 1

The effects of therapeutic drugs on the -SH/-SS ratio in the cell fraction of patient's cultured blood

| | | -SH/-SS ratio | | | | | | |
| --- | --- | --- | --- | --- | --- | --- | --- | --- |
| Drug | Dosage | Example 1 | Example 2 | Example 3 | Example 4 | Example 5 | Example 6 | Example 7 |
| Control | 0 | 2.00 | 1.17 | 1.00 | 0.93 | 2.00 | 1.52 | 1.24 |
| Ukrain, mg | 0.5 | 2.29 | 1.00 | 1.45 | 1.42 | 2.28 | — | — |
| | 2.5 | 2.00 | 0.50 | 1.14 | 1.20 | 2.55 | — | — |
| | 5.0 | 3.00 | 1.27 | 1.67 | 2.50 | 2.16 | — | — |
| | 10.0 | 1.75 | 1.75 | 1.38 | 2.00 | 2.11 | — | — |
| Oliphen, g | 0.05 | 1.89 | — | 1.22 | — | 2.35 | — | 1.45 |
| | 0.15 | 2.17 | — | 1.10 | — | 2.77 | — | 1.39 |
| | 0.5 | 2.83 | — | 1.35 | — | 3.12 | — | 0.93 |
| | 1.0 | 2.51 | — | 1.51 | — | 2.86 | — | 1.12 |
| Reaferon, $10^6$ U | 0.5 | — | 1.25 | — | — | — | 2.53 | — |
| | 1.0 | — | 1.50 | — | — | — | 3.07 | — |
| | 3.0 | — | 1.08 | — | — | — | 2.14 | — |
| | 6.0 | — | 1.03 | — | — | — | 1.79 | — |
| Cycloferon, g | 0.25 | — | — | — | 1.57 | — | 2.14 | 2.58 |
| | 0.5 | — | — | — | 1.94 | — | 2.66 | 2.18 |

The above experience proves that the method by the present invention is reasonably universal providing for testing drug in treatment of cancerous, viral, autoimmune, and other diseases. The time required for choosing an optimal drug by in vitro screening is 2–3 h.

I claim:

1. A method of selecting a drug for a patient suffering from a disease selected from the group consisting of cancer, viral diseases and autoimmune diseases comprising obtaining samples of heparinized whole blood from the patient;

determining the amount of sulfhydryl and disulfide groups in one of the samples of heparinized whole blood;

calculating the ratio of sulfyhdryl groups to disulfide groups for that sample of heparinized whole blood;

adding to a series of the remaining samples of heparinized whole blood drugs appropriate for the treatment of the disease at a dose in a ratio of to 1:5000 of the therapeutic dose of each drug;

incubating each drug in each sample of heparinized whole blood;

determining the amount of sulfhydryl and disulfide groups in each sample of heparinized whole blood to which a drug has been added;

calculating the ratio of sulfyhdryl groups to disulfide groups for each sample of heparinized whole blood to which a drug has been added;

selecting the drug to be administered to the patient that produced the greatest increase in the ratio of sulfhydryl groups to disulfide groups in a sample of heparinized whole blood from the patient.

2. A method according to claim 1, characterized in that incubating is performed for 1 h at 37° C.

* * * * *